United States Patent

Euteneuer et al.

[11] Patent Number: 5,147,302
[45] Date of Patent: Sep. 15, 1992

[54] METHOD OF SHAPING A BALLOON OF A BALLOON CATHETER

[75] Inventors: Charles L. Euteneuer, St. Michael; Peter T. Keith, Edina, both of Minn.

[73] Assignee: SciMed Life Systems, Inc., Maple Grove, Minn.

[21] Appl. No.: 341,430

[22] Filed: Apr. 21, 1989

[51] Int. Cl.⁵ ............................................. A61M 29/02
[52] U.S. Cl. ..................................... 604/103; 604/96; 606/191; 606/194
[58] Field of Search ............ 600/18; 604/96, 101–103, 604/191; 606/192–194, 96

[56] References Cited

U.S. PATENT DOCUMENTS

| | | | |
|---|---|---|---|
| 3,050,066 | 8/1962 | Koehn | 606/192 X |
| 4,276,874 | 7/1981 | Wolvek et al. | |
| 4,346,698 | 8/1982 | Hanson et al. | 600/18 |
| 4,573,470 | 3/1986 | Samson et al. | 128/344 |
| 4,576,142 | 3/1986 | Schiff | 600/18 |
| 4,710,181 | 12/1987 | Fuqua | 604/96 X |
| 4,771,776 | 9/1988 | Powell et al. | 128/344 |
| 4,820,349 | 4/1989 | Saab | 604/101 |
| 4,921,483 | 5/1990 | Wijay et al. | 604/96 |
| 4,941,877 | 2/1989 | Montano, Jr. | 604/96 |
| 4,952,357 | 8/1988 | Euteneuer | 264/129 |
| 5,087,246 | 2/1992 | Smith | 604/96 |

FOREIGN PATENT DOCUMENTS 74133 12/1987 Australia .
3124198 4/1982 Fed. Rep. of Germany .
2078114 6/1982 United Kingdom .

Primary Examiner—Robert A. Hafer
Assistant Examiner—Kerry Owens
Attorney, Agent, or Firm—Kinney & Lange

[57] ABSTRACT

The balloon of an angioplasty balloon catheter is prepared for insertion through a patient's cardiovascular system by a series of steps to create three or more folded wings or flaps. The wings are wrapped circumferentially to provide a minimized outer diameter when the balloon is in its deflated state.

34 Claims, 3 Drawing Sheets

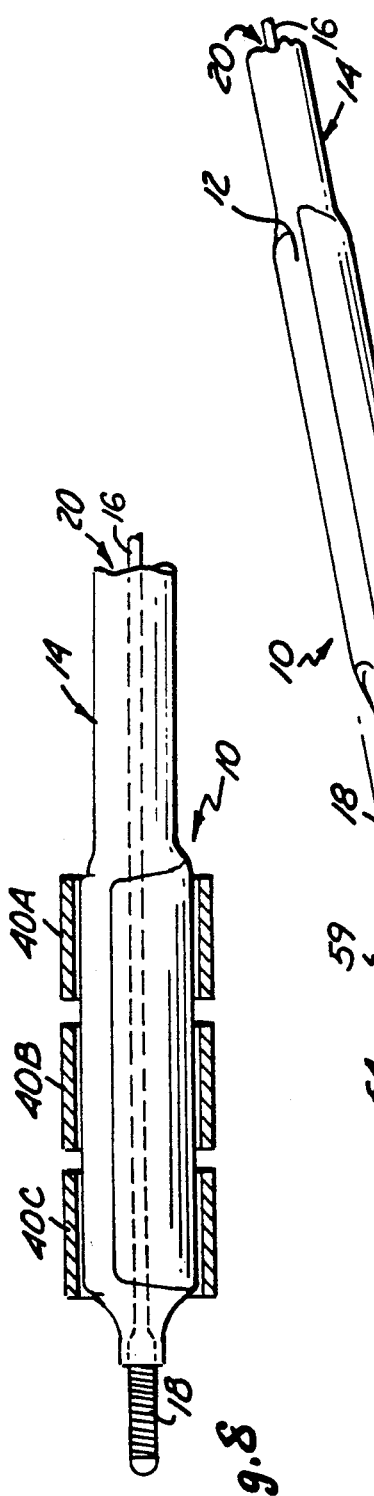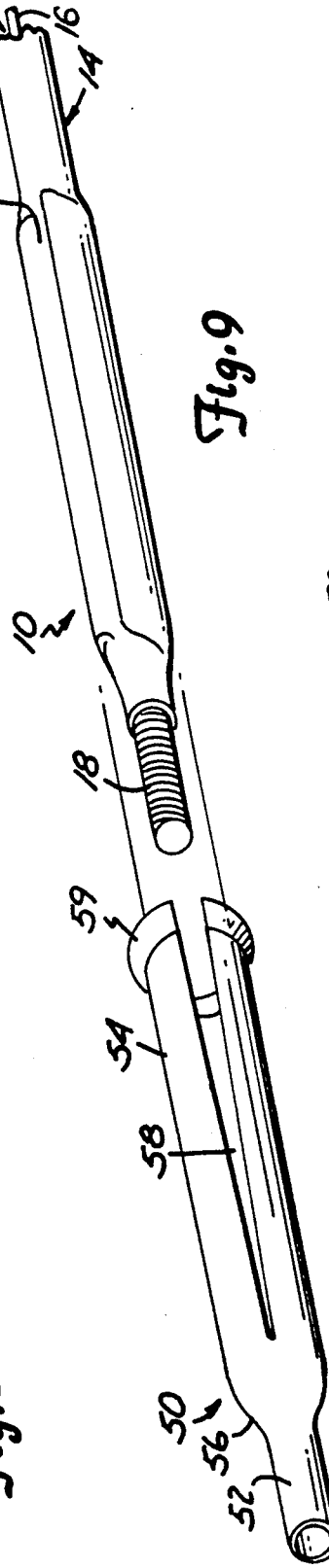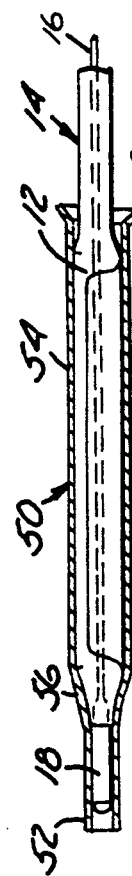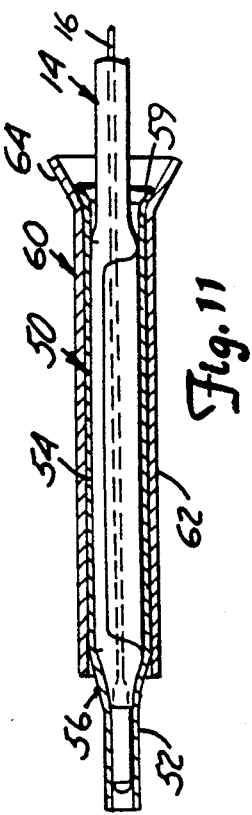

METHOD OF SHAPING A BALLOON OF A BALLOON CATHETER

REFERENCE TO COPENDING APPLICATION

Reference is hereby made to a copending application entitled "MULTIPART SPLIT SLEEVE BALLOON PROTECTOR FOR DILATATION CATHETER" by P. Keith which was filed on even date and which is assigned to the same assignee as the present application.

BACKGROUND OF THE INVENTION

1. Field of the Invention

The present invention relates to the field of angioplasty, and in particular to the preparation of dilatation balloon catheters to facilitate their insertion into and through the cardiovascular system of a patient.

2. Description of the Prior Art

Percutaneous transluminal coronary angioplasty (PTCA) is a procedure which is well established for the treatment of blockages in the coronary arteries. Blockages may occur from cholesterol precipitation on the coronary wall which may be in any stage from initial deposit through aged lesions. Coronary arteries can also become blocked due to formation of thrombus.

The most widely used form of percutaneous coronary angioplasty makes use of a dilatation balloon catheter. The catheter is inserted into the patient's vascular system and guided until the balloon at the distal end of the catheter is positioned across the stenosis. A radiographic contrast fluid is then fed under pressure through an inflation lumen of the catheter to the balloon, which causes the balloon to expand outward, thereby opening the stenosis.

One important characteristic of a dilatation balloon catheter used for angioplasty is its "profile", which is determined by the outer diameter of the distal end portion of the balloon when deflated. Considerable effort has been spent in developing low profile dilatation balloon catheters by minimizing the dimensions of the core or inner tube which extends through the balloon to its distal end, and by reducing wall thickness, to the extent possible, of the balloon itself.

This outer diameter affects the ease and ability of the dilatation catheter to pass through a guide catheter, through the coronary arteries, and across a tight lesion.

In order to reduce the outer diameter of the balloon in its deflated condition, it is common to fold the balloon flat, so that two wings or flaps are formed. These two wings are then brought together in some fashion so as to reduce the overall diameter of the deflated balloon. This is commonly done by installing a sleeve or balloon protector around the deflated balloon to bring the folds together. In actual use, when inflation fluid is applied to the folded balloon, it causes the flaps to unwrap so that the balloon can inflate to its full inflated state.

While it is desirable to minimize profile, it is also desirable to provide as large as possible an inflated outer diameter of the balloon relative to the detailed profile. One practical effect is that the two flaps formed when the balloon is deflated and prepared for wrapping (during balloon protector installation) become very large relative to the core or inner tube of the catheter. The result is that it is difficult to get these two "large" flaps to fold together and squeeze out all of the "dead" space between them when folded, without damaging the catheter during balloon protector installation. The lowest deflated profile from a balloon results when the wings are folded in a manner that removes all of the interstitial space between the wings. Thus a relatively large deflated outer diameter of the balloon typically results. There is a continued need for improvements in catheter constructions and preparation techniques which achieve low profile and large inflated balloon diameters without sacrificing other characteristics.

SUMMARY OF THE INVENTION

In the present invention, reduced deflated-state outer diameter characteristics in a balloon dilatation catheter are achieved by providing at least three folded flaps or wings when the balloon is in a deflated state. By using three or more wings, the dimension of each wing is minimized. As a result, when the wings or flaps are wrapped circumferentially, the distance that each flap extends around the catheter in the circumferential direction is reduced when compared to the conventional dilatation balloon configuration using a pair of flaps, and the ease of which those flaps fold is enhanced. The result is a reduced outer diameter given the same profile and outer diameter of the balloon in the inflated state.

In one embodiment of the invention, the N-flap balloon configuration (in which N is at least three) is formed by clamping a folded portion of a deflated balloon, and then inflating the remaining unclamped portion of the balloon. The inflated portion is then deflated while applying pressure to the unclamped portion to form at least two additional folded flap portions.

BRIEF DESCRIPTION OF THE DRAWINGS

FIGS. 7 and 8 show steps of wrapping and initial heat set of the tri-fold balloon.

FIGS. 9-11 show steps of application of a balloon protector to the wrapped balloon.

DETAILED DESCRIPTION OF THE PREFERRED EMBODIMENTS

Figure 1:
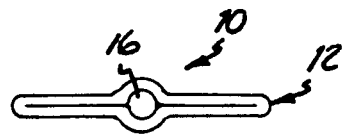
FIGS. 1-4 show steps of a first method for tri-folding the balloon of a dilatation balloon catheter.

Tri-fold dilatation balloon catheter 10 of the present invention has an inflatable balloon 12 mounted at the distal end of hollow flexible shaft 14. Core member 16 extends through the interior of balloon 12 and has a spring coil tip 18 at its distal end. The distal end of balloon 12 is bonded to core 16. Inflation lumen 20 extends through the interior of shaft 14 and communicates with the interior of balloon 12. The proximal end of shaft 14, which is not shown, is preferably connected to a manifold, which in turn is capable of connection to an inflation device so that fluid pressure can be applied through inflation lumen 20 to the interior of balloon 12. By applying positive fluid pressure, balloon 12 is inflated so that it has a circular cross-sectional inflated configuration. By applying negative fluid pressure (for example, by drawing a vacuum at the proximal end of shaft 20), balloon 12 is collapsed to its deflated condition in which it has three flaps or wings 12A-12C which are tightly wrapped in a circumferential direction around core 16.

FIGS. 1-4 illustrate one method of the formation of wings 12A-12C. In FIG. 1, balloon 12 is collapsed by the application of a vacuum to inflation lumen 20 so that a flat wing configuration is produced. Core 16 is in the center of the flat winged configuration shown in FIG. 1.

Figure 2:
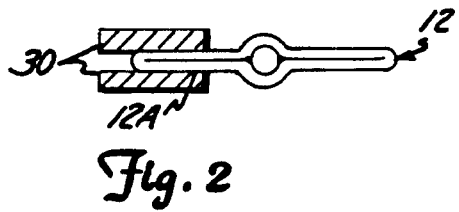

In FIG. 2, clamping fixture 30 is used to clamp approximately one-third of the distance across balloon 12. Clamp 30 is made of a material which will not tear, puncture, or otherwise damage balloon 12.

Figure 3:
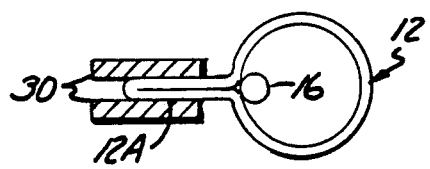

As illustrated in FIG. 3, balloon 12 is then inflated at low pressure while clamp 30 holds wing 12A. The unclamped portion of balloon 12, therefore, is reinflated.

Figure 4:
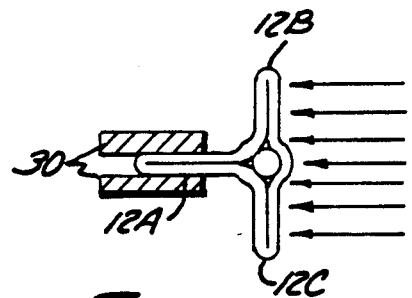

In FIG. 4, pressure is applied to the exterior of unclamped portion of balloon 12 while pulling a vacuum through inflation lumen 20, so that the unclamped portion of balloon 12 is deflated while being pressed against the side of clamp 30. This forms wings 12B and 12C. The result is a three wing configuration which generally has a T-shaped cross-section as shown in FIG. 4.

Figure 5:
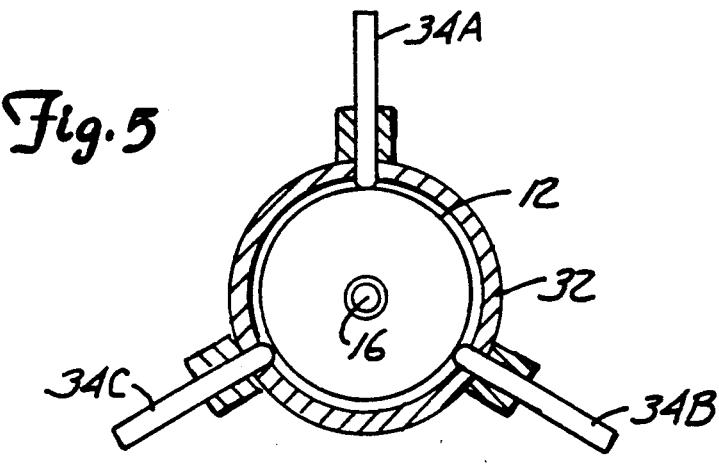
FIGS. 5 and 6 show steps of a second method of tri-folding the balloon of a dilatation balloon catheter.
Figure 6:
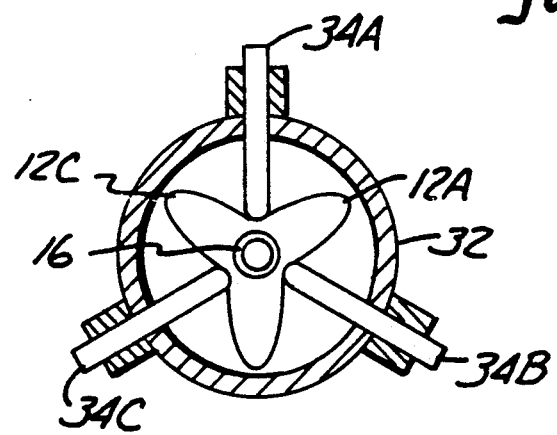

FIGS. 5 and 6 illustrate another method of achieving a trifold state of the balloon. Balloon 12 is initially pressurized to a low pressure and centered within tubular fixture 32. Moveable blades 34A-34C, which are supported by and moveable with respect to FIGS. 32, are initially in the retracted position as shown in FIG. 5. Blades 34A-34C have a length which is approximately equal to the length of balloon 12, and are circumferentially spaced at 120° intervals.

As illustrated by FIG. 6, blades 34A-34C are simultaneously moved radially inward toward core 16. Blades 34A-34C do not, however, come in contact with core 16 in order to avoid damage to balloon 12. A vacuum is pulled through lumen 20 to cause formation of wings 12A-12C. While the vacuum is maintained, blades 34A-34C are returned to their retracted position and balloon 12 is removed from fixture 32.

Once the trifold configuration has been formed (such as by the method of FIGS. 1-4 or the method of FIGS. 5 and 6), balloon 12 is ready for a wrapping and initial heat set procedure. This is illustrated in FIGS. 7 and 8.

Figure 7:
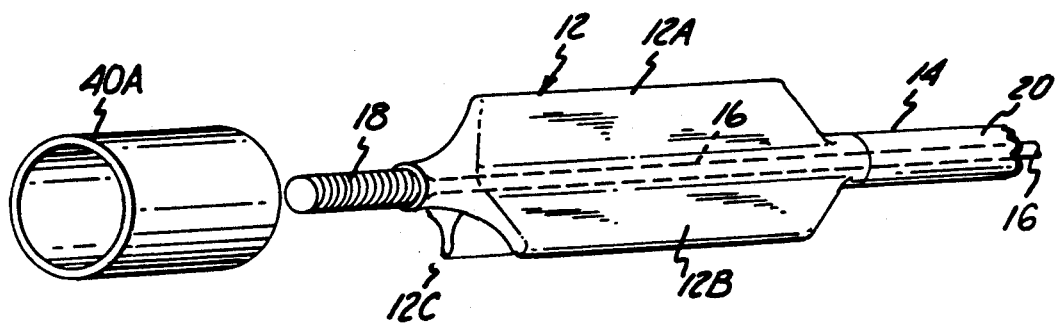

In the procedure shown in FIGS. 7 and 8, three relatively large inside diameter tube segments 40A-40C are advanced, one at a time, from the distal end of catheter 10 over balloon 12. These tube segments 40A-40C initiate wrapping of the three wings or flaps 12A-12C of balloon 12. The inside diameters of tube segments 40A-40C are just large enough to assure the core 16 will not buckle as tube segments 40A-40C are advanced over balloon 12. Using multiple segments 40A-40C reduces the frictional force build up which would occur if a single tube having a length equal to the total length of balloon 12 were applied. In addition, this allows the first segment 40A, once it is near the middle of balloon 12, to be pulled rather than pushed over the proximal balloon cone.

Once segments 40A-40C are in place and balloon 12 is partially folded as shown in FIG. 8, catheter 10 is subjected to a heat treatment at approximately 50° C. to heat set balloon 12. After the initial heat treatment, tube segments 40A-40C are removed from balloon 12. The initial heat treatment has caused the wings 12A-12C to fold or wrap further around core 16, so that balloon 12 is more tightly wrapped than it was prior to the heat treatment. This initial wrapping and setting facilitates ease of installation of the final balloon protectors.

As shown in FIG. 9, the next step involves applying inner balloon protector sleeve 50 over the distal end of catheter 10. Inner balloon protector sleeve 50, is shown in FIG. 9, includes a narrow distal portion 52 and a wider proximal portion 54, with shoulder 56 connecting distal portion 52 to proximal portion 54.

Distal portion 52 of inner balloon protector sleeve 50 has an inner diameter which is slightly larger than the outer diameter of tip 18 of catheter 10. The length of distal portion 52 is approximately equal to the length by which tip 18 extends distally from the distal end of balloon 12.

Proximal portion 54 of inner balloon protector sleeve 50 has a length which is approximately equal to the length of balloon 12 and has a longitudinally extending expansion slit 58 which extends from the proximal end of inner balloon protector sleeve 50 substantially the entire length of proximal section 54. Inner balloon protector 50 also has a flange or flare 59 at its proximal end to reduce abruptness of the leading edge of inner protector 50 as it is urged onto balloon 12. The inner diameter of proximal section 54, when expansion slit 58 is closed, is slightly larger than the minimum profile diameter achievable for balloon 12 in its deflated condition.

Inner balloon protector sleeve 50 is applied over balloon 12 of catheter 10 by moving sleeve 50 in a proximal direction, starting at tip 18 at the distal end of catheter 10, while a vacuum is applied to balloon 12 through lumen 20. Sleeve 50 is gently urged over balloon 12 as sleeve 50 is moved in a proximal direction relative to catheter 10. Sleeve 50 must be aligned so that none of the wings 12A-12C project out of sleeve 50 through slit 58. Expansion slit 58 provides proximal sleeve portion 54 with a variable inner diameter, which reduces the force required to apply sleeve 50 onto balloon 12 by reducing friction between balloon 12 and the inner wall of sleeve 50. This ensures that balloon 12 will not be torn and that core 16 will not be crushed or bent during application of sleeve 50.

FIG. 11 shows the next step in which outer balloon protector sleeve 60 is applied over inner balloon protector sleeve 50. Sleeve 60 slides over narrow distal section 52 of inner balloon protector sleeve 50 and then over the wider proximal section 54 of sleeve 50 until it reaches the position shown in FIG. 11.

Outer balloon protector sleeve 60 has a main tubular body portion 62 and a flange or lip section 64 at its proximal end. The inner diameter of outer balloon protector sleeve 60 is about 0.001 inch smaller than the outer diameter of the inner balloon protector proximal section 54. This causes expansion slit 58 to be closed when outer balloon protector sleeve 60 is applied over inner balloon protector sleeve 50, as well as overall compression of inner balloon protector sleeve 50.

As outer balloon protector sleeve 60 is applied over inner balloon protector sleeve 50, the narrow distal section 52 of inner balloon protector sleeve 50 may be grasped such that force due to friction during application is transferred between outer and inner balloon protector sleeves 60 and 50 and not to any portion of balloon catheter 10. As expansion slit 58 is closed and forced together by outer balloon protector sleeve 60, balloon flaps 12A-12C become more tightly wrapped.

After both sleeves 50 and 60 are in place over the distal end portion of catheter 10, a heated sterilization cycle is performed. This causes balloon 12 to be heat set in its further definitive compressed form. The heat setting of balloon 12 provides a "memory" to balloon 12 so that when inner and outer balloon protector sleeves 50 and 60 are removed, prior to use balloon 12 will remain in its tightly- wrapped, compressed form. Even after balloon 12 has been inflated, when it is again deflated it will tend to return to substantially the same shape that it had during the heat sterilization process. Therefore, small profiles can be achieved even after balloon inflation.

In a preferred embodiment of the present invention, the inner and outer sleeves 50 and 60 are a heat shrinkable material which also will not stick to catheter 10 (and particularly to balloon 12). One preferred material for segments 40A-40C, and protector sleeves 50 and 60 is polytetrafluoroethylene.

The outer diameter of balloon 12 may be further reduced if additional heat setting steps and tighter balloon protector systems are alternately installed to stepwise achieve tighter and tighter compressions. The new balloon protector sleeves have smaller diameters than those of the previous sleeves. By repeating the steps of applying the balloon protector sleeves and performing a heat setting step, while using successively smaller and smaller sets of inner and outer sleeves, balloon 12 is treated until it reaches the desired profile and deflated outer diameter.

Alternately, the tri-tube segment application operation (FIGS. 7 and 8) can be repeated, after the heat setting, with smaller diameter segments to achieve low profile in successive fashion. The final result is a balloon with several small adjacent segments (as small as achieveable) covering the balloon.

Balloon catheters using three or more wings or flaps wrapped circumferentially around the lumen offer a reduced deflated balloon diameter without requiring a corresponding decrease in the diameter of the inflated balloon. Further, by using more than two flaps in the deflated balloon, the balloon will inflate more smoothly and with less radial and circumferential motion as the flaps unwrap from their wrapped position and dilate the lesion.

Although the present invention has been described with reference to preferred embodiments, workers skilled in the art will recognize that changes may be made in form and detail without departing from the spirit and scope of the invention.

We claim:

1. A method of shaping a balloon of a balloon catheter when the balloon is in a deflated state and includes a member extending longitudinally through the balloon, the method comprising:
    inflating at least a portion of the balloon;
    applying external pressure to the balloon in a generally radially inward direction;
    deflating the balloon to form at least three folded wings;
    applying a cover over the balloon which causes the wings to wrap around the member, the cover including a plurality of tubes, each having a length which is less than a length of the balloon; and
    subjecting the balloon to a heat treatment at an elevated temperature with the tubes of the cover in place.

2. The method of claim 1 and further comprising:
    removing the tubes of the cover after heat treatment; and
    sliding a balloon protector longitudinally over the wrapped balloon while applying a vacuum thereto.

3. The method of claim 2 wherein the balloon protector includes a longitudinal expansion slit therealong to facilitate placement over the wrapped balloon.

4. The method of claim 3 and further comprising:
    applying an outer balloon protector over the balloon protector with the expansion slit.

5. The method of claim 1 wherein the balloon is of a material which is heat set by the heat treatment.

6. The method of claim 1 and further comprising:
    after heat treatment, replacing the tubes of the cover with a balloon protector.

7. The method of claim 6 and further comprising:
    further compressing the folded wings by applying an outer balloon protector over the balloon protector.

8. The method of claim 7 and further comprising:
    subjecting the balloon and balloon protectors thereon to a second heat treatment.

9. A method of shaping a balloon of a balloon catheter when the balloon is in a deflated state, the method comprising:
    inflating at least a portion of the balloon;
    applying external pressure to the balloon in a generally radially inward direction;
    deflating the balloon to form at least three folded wings;
    clamping a first portion of the balloon to form a first folded wing prior to inflating at least a second portion of the balloon; and
    wherein applying external pressure and deflating forms second and third folded wings.

10. The method of claim 9 wherein the balloon catheter includes a member extending longitudinally through the balloon, and further comprising:
    wrapping the folded wings around the member.

11. The method of claim 10 and further comprising:
    applying a balloon protector over the deflated balloon which causes the wings to wrap around the member.

12. The method of claim 11 and further comprising:
    subjecting the balloon to an elevated temperature with the balloon protector in place over the balloon.

13. The method of claim 12 wherein the balloon is of a material which is heat set by the heat treatment.

14. The method of claim 10 wherein wrapping comprises:
    applying a cover over the balloon which causes the wings to wrap around the member; and
    subjecting the balloon to a heat treatment at an elevated temperature with the cover in place.

15. The method of claim 14 wherein the balloon is of a material which is heat set by the heat treatment.

16. A method of shaping a balloon of a balloon catheter which has a core member extending longitudinally through the balloon, the method comprising:
    clamping a part of the balloon to form a first wing portion;
    inflating the balloon:
    pinching the balloon while deflating the balloon to form at least two additional wing portions; and
    wrapping the wing portions around the core member.

17. The method of claim 16 and further comprising:
    applying a cover over the wrapped wing portions of the balloon.

18. The method of claim 17 and further comprising:
    subjecting the balloon to an elevated temperature with the cover in place over the balloon.

19. The method of claim 17 wherein the cover includes a plurality of tubes.

20. The method of claim 19 wherein each tube has a length which is less than a length of the balloon.

21. The method of claim 17 wherein the cover has a longitudinal slit therein.

22. A method of shaping a balloon of a balloon catheter which has a core member extending longitudinally through the balloon, the method comprising:

forming at least three folded wings in the balloon in a deflated condition; and applying a cover over the balloon which causes the wings to wrap around the member, the cover including a plurality of tubes, each having a length which is less than a length of the balloon.

23. The method of claim 22 and further comprising:

subjecting the balloon to a heat treatment at an elevated temperature with the cover in place over the balloon.

24. The method of claim 23 wherein the balloon is of a material which is heat set by the heat treatment.

25. The method of claim 22 and further comprising:

after heat treatment, replacing the tubes of the cover with a balloon protector.

26. The method of claim 25 and further comprising:

further compressing the folded wings by applying an outer balloon protector over the balloon protector.

27. The method of claim 26 and further comprising:

subjecting the balloon and balloon protectors thereon to a second heat treatment.

28. A method of shaping a balloon of a balloon catheter which has a core member extending longitudinally through the balloon, the method comprising:

inflating the balloon;

deflating the balloon while applying external force to the balloon at a plurality of circumferentially spaced positions to form at least three folded wings in the balloon; and wrapping the folded wings around the core member.

29. The method of claim 28 wherein wrapping comprises:

applying a cover over the balloon which causes the folded wings to wrap around the member.

30. The method of claim 29 wherein the cover includes a longitudinal slit therethrough.

31. The method of claim 28 wherein wrapping comprises:

applying a cover over the balloon which causes the folded wings to wrap around the member; and subjecting the balloon to a heat treatment at an elevated temperature with the cover in place.

32. The method of claim 31 wherein the balloon is of a material which is heat set by the heat treatment.

33. The method of claim 29 wherein the cover includes a plurality of tubes, each having a length which is less than a length of the balloon.

34. The method of claim 31 wherein the wrapping further comprises:

removing the cover after the heat treatment;

applying a second smaller cover over the balloon which causes the folded wings to wrap even tighter around the member; and subjecting the balloon to a second heat treatment at an elevated temperature with the second cover in place.

* * * * *